United States Patent
True-Dahl et al.

(10) Patent No.: US 8,496,816 B2
(45) Date of Patent: Jul. 30, 2013

(54) MODULAR FUEL FILTER ASSEMBLY

(75) Inventors: Abby True-Dahl, Sparta, TN (US);
Gerard Malgorn, Quimper (FR);
Arnuad LeVen, Ergue Gaberic (FR);
Gildas LeMen, Guengat (FR); Mark Wieczorek, Cookeville, TN (US);
Zemin Jiang, Cookeville, TN (US);
Jeffrey A. Husband, Cookeville, TN (US); Ismail C. Bagci, Cookeville, TN (US); Charles W. Hawkins, Sparta, TN (US); Chad M. Thomas, Algood, TN (US); Mark Johnson, Cookeville, TN (US); Ted Loftis, Cookeville, TN (US);
Robert A. Bannister, Stoughton, WI (US)

(73) Assignee: Cummins Filtration IP, Inc., Minneapolis, MN (US)

( * ) Notice: Subject to any disclaimer, the term of this patent is extended or adjusted under 35 U.S.C. 154(b) by 1229 days.

(21) Appl. No.: 12/284,685

(22) Filed: Sep. 24, 2008

(65) Prior Publication Data

US 2009/0078631 A1 Mar. 26, 2009

Related U.S. Application Data

(60) Provisional application No. 60/994,993, filed on Sep. 24, 2008.

(51) Int. Cl.
*B01D 35/18* (2006.01)
*B01D 27/00* (2006.01)
*B01D 35/00* (2006.01)

(52) U.S. Cl.
USPC .......... 210/175; 73/53.01; 210/184; 210/435; 210/454; 123/557; 219/209

(58) Field of Classification Search
None
See application file for complete search history.

(56) References Cited

U.S. PATENT DOCUMENTS

| | | | |
|---|---|---|---|
| 3,235,084 A | 2/1966 | King et al. | |
| 4,372,279 A * | 2/1983 | Parks | 123/557 |
| 4,424,422 A | 1/1984 | Bell et al. | |
| 4,470,301 A * | 9/1984 | Hutchins et al. | 73/304 R |
| 4,585,924 A | 4/1986 | Pakula | |
| 4,596,224 A | 6/1986 | Prager | |
| 4,790,285 A | 12/1988 | Wolf | |
| 4,818,842 A | 4/1989 | Walty | |
| 5,156,135 A | 10/1992 | Snyder | |
| 6,207,045 B1 * | 3/2001 | Jiang | 210/86 |

(Continued)

OTHER PUBLICATIONS

International Search Report of PCT/US2008/011074, dated Mar. 18, 2009.

(Continued)

*Primary Examiner* — Dirk Bass
(74) *Attorney, Agent, or Firm* — Hamre, Schumann, Mueller & Larson, P.C.

(57) ABSTRACT

A fuel heater module and a water-in-fuel sensor module are disclosed that are configured to be connected to an outside surface of a filter assembly. The fuel heater module includes an inlet port and an outlet port with a heating element positioned in the fluid path between the inlet and outlet. A thermostat is included for controlling operation of the heating element. The water-in-fuel sensor module is configured to detect water in the filter housing that it may be drained from the filter housing. Both modules are configured to be attached to an outside surface of the filter housing thereby being readily replaceable.

13 Claims, 19 Drawing Sheets

U.S. PATENT DOCUMENTS

| | | | |
|---|---|---|---|
| 6,358,416 B1 * | 3/2002 | Miller et al. | 210/248 |
| 6,795,646 B1 | 9/2004 | Wieczorek et al. | |
| 6,939,464 B1 * | 9/2005 | Jiang et al. | 210/232 |
| 2005/0005584 A1 * | 1/2005 | Decaux | 55/423 |

OTHER PUBLICATIONS

Extended European Search Report for European patent application No. 08834534.3, dated Sep. 27, 2010 (8 pages).

* cited by examiner

MODULAR FUEL FILTER ASSEMBLY

CROSS-REFERENCE TO RELATED APPLICATIONS

The present application claims the benefit of U.S. Patent Application No. 60/994,993 filed Sep. 24, 2008, which is incorporated herein by reference in its entirety.

FIELD OF THE INVENTION

The present invention relates generally to fuel filters and more particularly, to a fuel filter assembly utilizing detachable heating element modules and water-in-fuel sensor modules with built in draining capabilities.

BACKGROUND

In the field of diesel engine technology, it is common to use fuel injection systems. Such fuel injection systems include small, closely tolerated apertures and clearances with precision machining and matching of cooperating components. The proper function of these components and of the fuel injection system generally depends, in part, on the fuel reaching these components being free of contaminants, such as particulates and water. If the fuel is not adequately or properly filtered, the fuel injection system components are exposed to possible damage and subjected to premature wear. Other concerns with the delivery and use of fuel which is not adequately or properly filtered include inefficient combustion, high fuel consumption, poor starting, rough idle, and reduced engine power.

In addition to particulates, water in fuel has a direct impact on the service life and performance of diesel engines. Besides decreasing engine life, water can damage engine components and drastically increase down time and maintenance costs. Unfortunately, there is no way to prevent water from contaminating fuel as condensation is constantly formed during transport and storage. Further, heating fuel prior to its introduction into the combustion chamber increases the efficiency of diesel engines. Filter modules need low cost components that are standard in the product line to reduce time to market. These components need to offer flexible integration for accommodating a variety of customer requirements and space constraints.

SUMMARY

One embodiment according to the present invention discloses a unique fuel filter assembly. Other embodiments include unique apparatuses, systems, devices, methods, and combinations of these for detachably connecting modules of a fuel filter assembly to a filter housing. Further embodiments, forms, objects, features, advantages, aspects, and benefits of the present invention shall become apparent from the following description and drawings.

BRIEF DESCRIPTION OF THE DRAWINGS

FIG. 2b illustrates a rear view of the representative fuel filter heater module depicted in FIG. 2a.

DESCRIPTION OF THE ILLUSTRATIVE EMBODIMENTS

Figure 1:
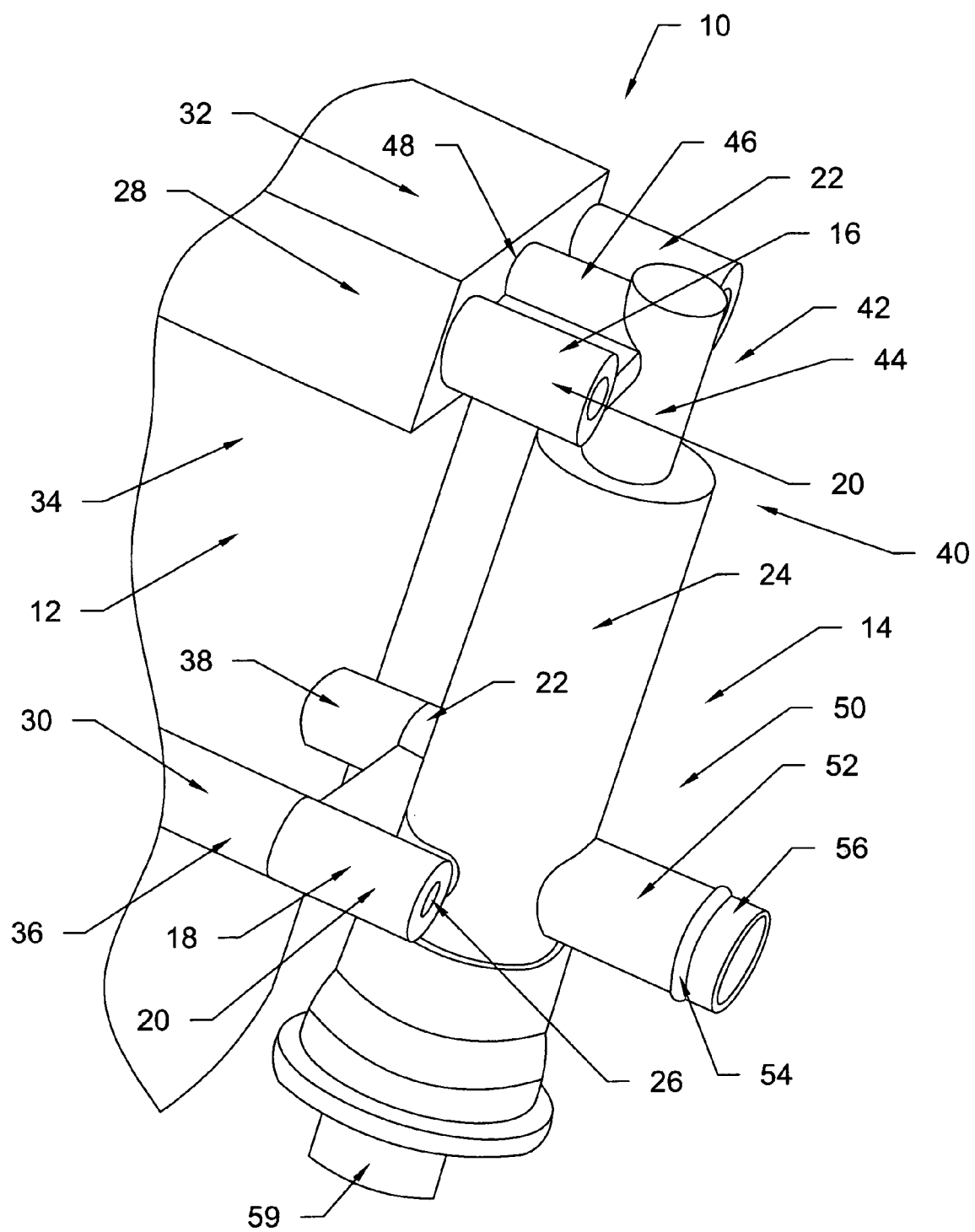
FIG. 1 illustrates a fuel filter heater module connected with a fuel filter housing.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention is illustrated therein being contemplated as would normally occur to one skilled in the art to which the invention relates.

Referring to FIG. 1, a partial fuel filter assembly 10 is illustrated that includes a main filter housing 12 and a detachable heating element module 14. Filter housing 12 includes one or more filtering elements configured and arranged to remove particulates and water from a flow of fuel. Heating element module 14 includes an upper attachment portion 16 and a lower attachment portion 18. Each attachment portion 16, 18 include a first and second attachment member 20, 22. In this form, attachment members 20, 22 have a generally cylindrical shape and protrude outwardly along a horizontal axis in relation to a main body 24. Attachment members 20, 22 include an aperture 26 that runs horizontally through the interior body of the attachment members 20, 22. Although not illustrated because they are recessed in apertures 26, a plurality of connectors, such as screws or bolts for example, are used to removably attach or connect heating element module 14 to filter housing 12.

Filter housing 12 includes an upper filter attachment portion 28 and a lower filter attachment portion 30 that are configured and arranged to line up with upper and lower attachment portions 16, 18 of detachable heating element module 14. As illustrated, upper filter attachment portion 28 is configured as a generally rectangular shaped attachment member 32 that protrudes outwardly along a horizontal axis from a side surface 34 of filter housing 12. Lower filter attachment portion 30 is configured as first and second contacts 36, 38 that protrude outwardly from side surface 34 of filter housing 12. Screws or bolts positioned in apertures 26 of heating element module 14 detachably connect heating element module 14 to filter housing 12.

An upper portion 40 of main body 24 includes an elbow shaped fluid output port 42. Output port 42 includes a vertical segment 44 and a horizontal segment 46 that is removably connected with a fluid input port 48 of filter housing 12. A lower portion 50 of heating element module 14 includes a fluid input port 52 that protrudes outwardly from the side of main body 24 along a horizontal axis. Output port 42 and the input port 52 are generally cylindrical in shape and input port 52 feeds fuel into main body 24 and output port 42 directs fuel to filter housing 12. Output port 42 creates a fluid path between heating element module 14 and filter housing 12. Input port 52 includes a rib 54 and a connection portion 56. Rib 54 acts as an abutment surface when a fuel line is connected with connection portion 56 of input port 52.

In this form, an electrical connector 59 is connected to a lower surface of main body 24. Although not illustrated in FIG. 1, main body 24 houses a heating element 58 and a thermostat. See FIGS. 5 and 6. Heating element 58 is used to heat fuel that enters main body 24. Electrical connector 59 is used to control heating element 58 as a function of readings received from thermostat 60. Some types of fuel, such as diesel fuel for instance, become viscous the colder it becomes. As such, the fuel is heated before entering filter housing 12 to ensure that it has the proper viscosity. Thermostat 60 is used to regulate the operating temperature of heating element 58 so that the fuel is maintained at a desired temperature level. In one form, thermostat 60 does this by controlling the flow of electrical current into heating element 58. Connection terminals 62 provide electrical energy to heating element 58, which causes heating element 58 to generate heat. See e.g. FIGS. 5 and 6.

Figure 2A:
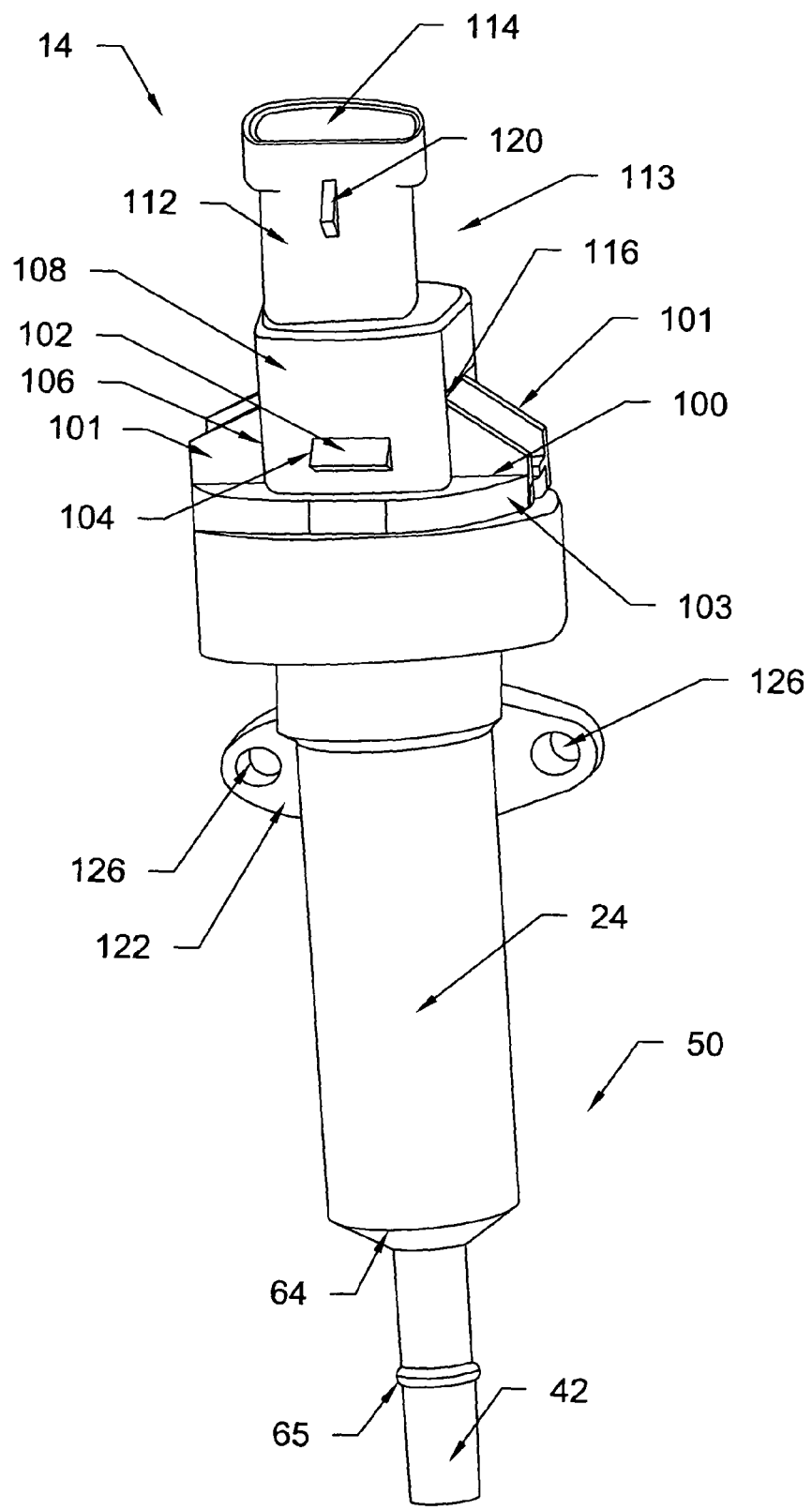
FIG. 2a illustrates another representative fuel filter heater module configured to be connected to a fuel filter housing.
Figure 2B:
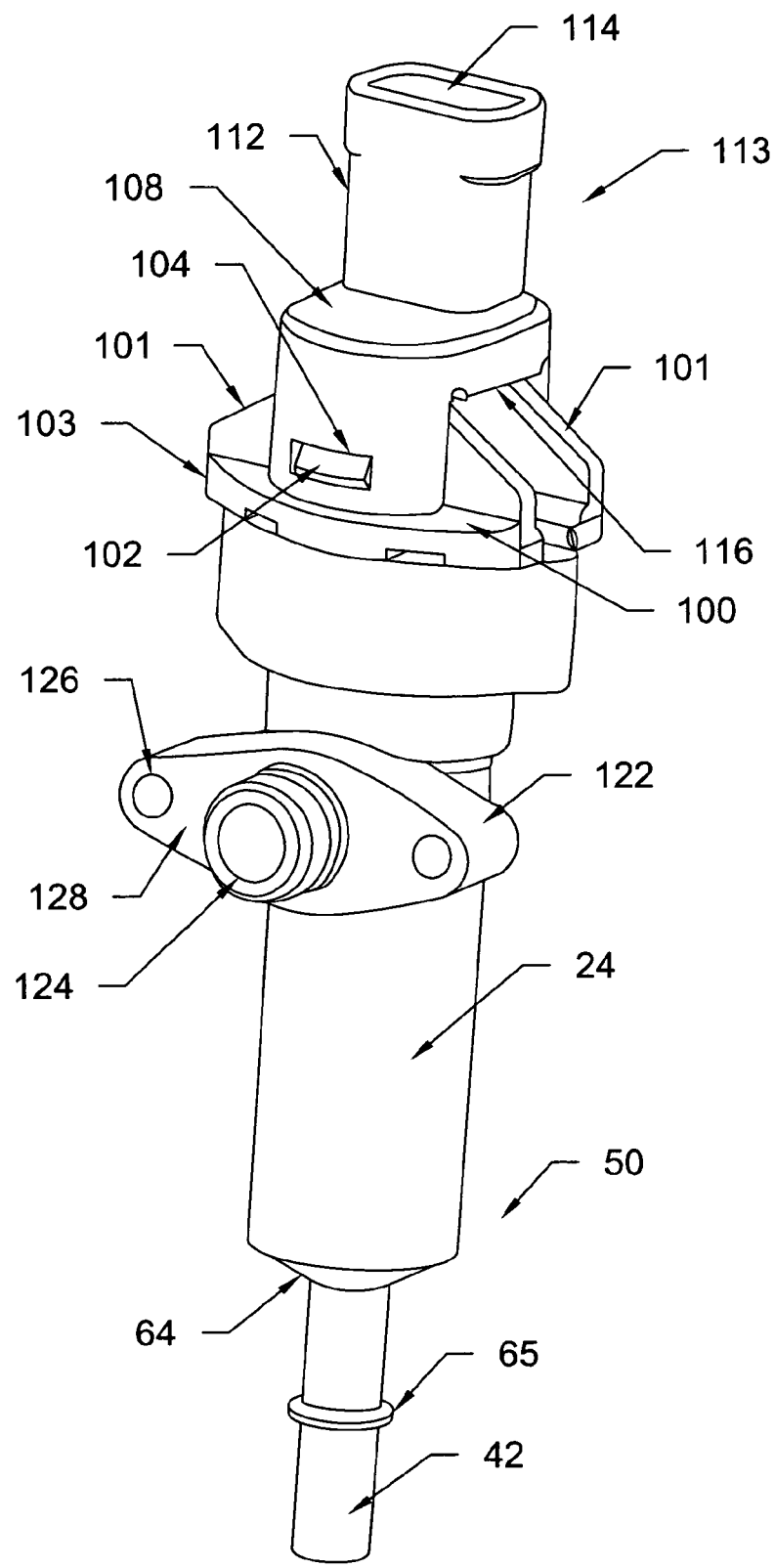

Referring to FIGS. 2a-2b, another representative detachable heating element module 14 is depicted. In this form, heating element module 14 includes a fluid input port 42 located at the lower portion 50 of main body 24. Input port 42 is generally cylindrical in shape and extends vertically from a lower surface 64 of main body 24. Input port 42 includes a ribbed portion 65 for abutment with a fuel supply line. Heating element module 14 includes an upper mounting bracket 100 that includes a pair of upwardly or vertically extending opposing mounting members 101 that extend from a base portion 103 of upper mounting bracket 100. In one form, upper mounting bracket 100 is detachably connected with main body 24. A pair of clips 102 extends horizontally from opposing mounting members 101. As illustrated, clips 102 snap into clip receiving apertures 104 in a lower portion 106 of a heating element housing 108. As such, heating element housing 108 is capable of being unsnapped and replaced if necessary.

Although not specifically illustrated in this form, in one form heating element housing 108 contains a heating element 58 and thermostat 60. See e.g. FIG. 5. In this illustrative form, heating element 58 and thermostat 60 extend downwardly into main body 24 of heating element module 14 in the fluid path between inlet port 42 and outlet port 124. A pair of connection terminals 62 is positioned within a neck portion 112 of an electrical connector 113 of heating element housing 108. See e.g. FIG. 6. In this form, connection terminals 62 are recessed within a recess 114 of neck portion 112.

Heating element housing 108 also includes a U-shaped notch portion 116 that fits over opposing mounting members 101 of upper mounting bracket 100. Neck portion 112 of heating element housing 108 also includes a clip attachment member 120 that allows a clip of a power and control connector to securely stay fastened to electrical connector 113. Main body 24 includes an attachment member 122 that is used to detachably mount main body 24 to a filter housing 12. See e.g. FIG. 1. Attachment member 122 include apertures 126 configured to receive a fastener, such as a screw or bolt, to securely, but detachably, connect main body 24 of heating element module 14 to filter housing 12.

As illustrated in FIG. 2b, heating element module 14 includes a fluid output port 124. In this form, output port 124 is located on and extends outwardly from a side surface 128 of attachment member 122. As such, during operation fluid enters through input port 42 where it travels into main body 24. As previously set forth, main body 24 houses heating element 58 which is configured to heat the fluid or fuel to a regulated temperature value. Thermostat 60 controls the operation of heating element 58 to predetermined temperature values to raise the temperature of the fuel to the desired or preferred temperature level. The fuel then travels out of main body 24 via output port 124 where it enters filter housing 12 to be filtered by one or more filters located in filter housing 12. As set forth above, each component of heating element module 14 is readily detachable from main body 24 thereby eliminating the need to replace the entire module as a whole should a particular component become faulty. For example, heating element housing 108 is configured to be unclipped from clips 102 thereby allowing selective removal of heating element 58 and thermostat 60 from main body 24 of heating element module 14.

Figure 3:
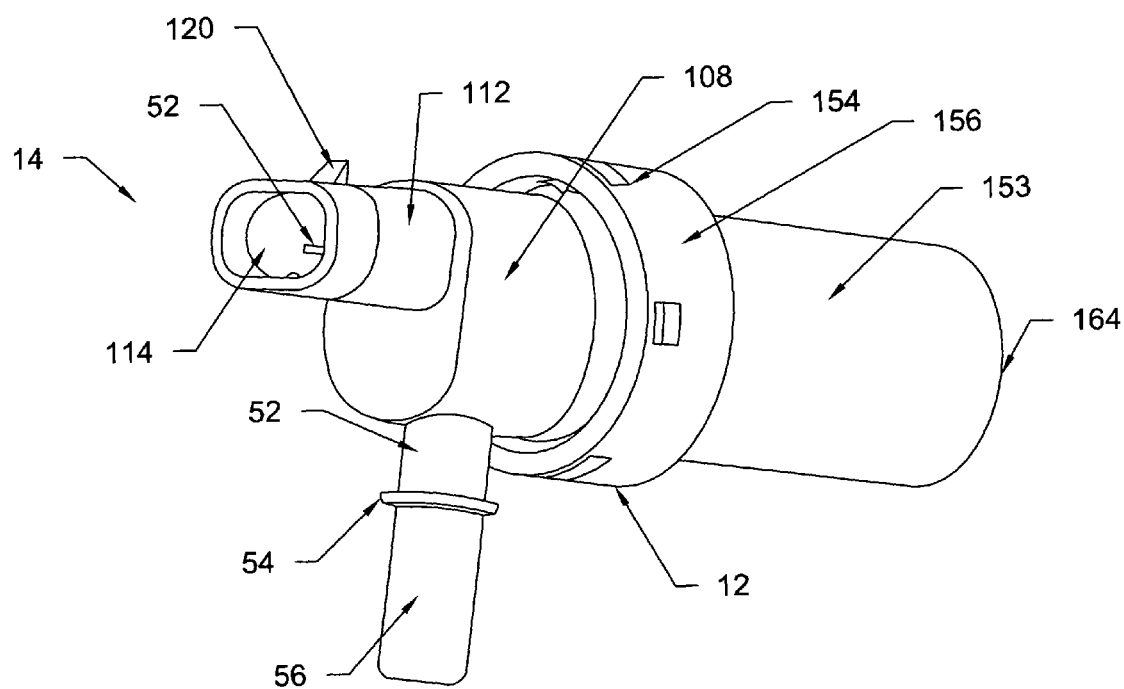
FIG. 3 illustrates a heating element housing connected with a main body.
Figure 4:
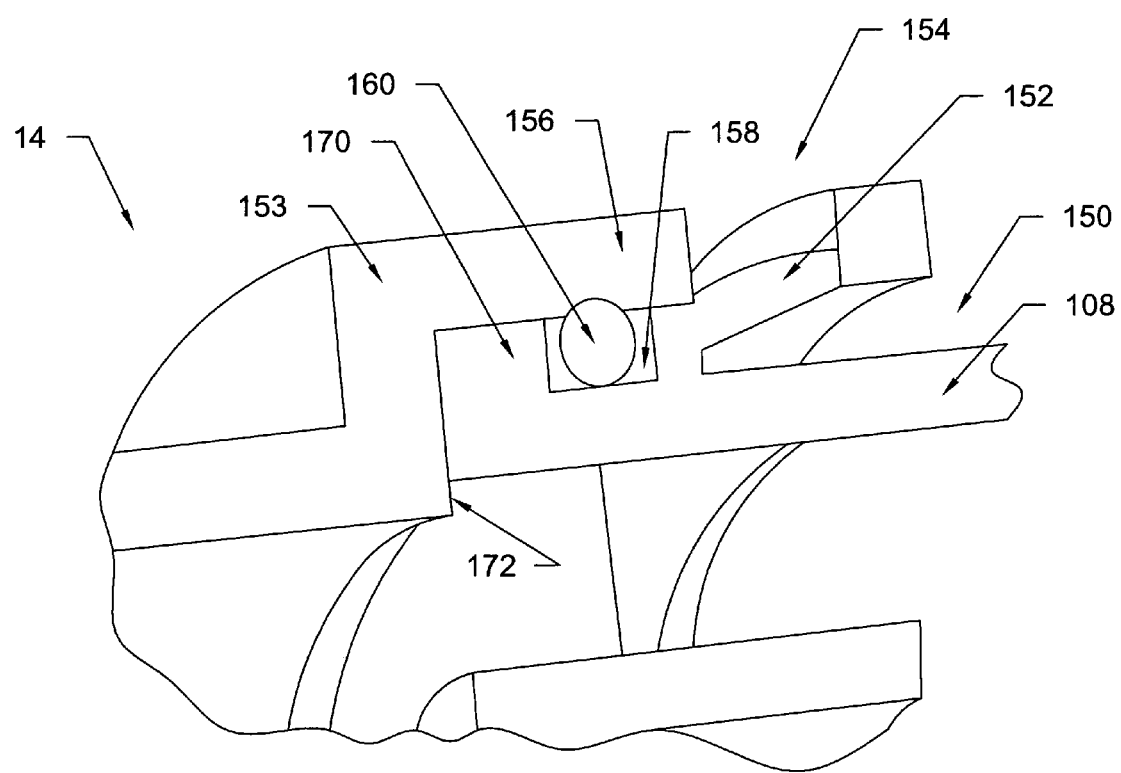
FIG. 4 is a cross-sectional view of a portion of the heat element housing and main body illustrated in FIG. 3.
Figure 5:
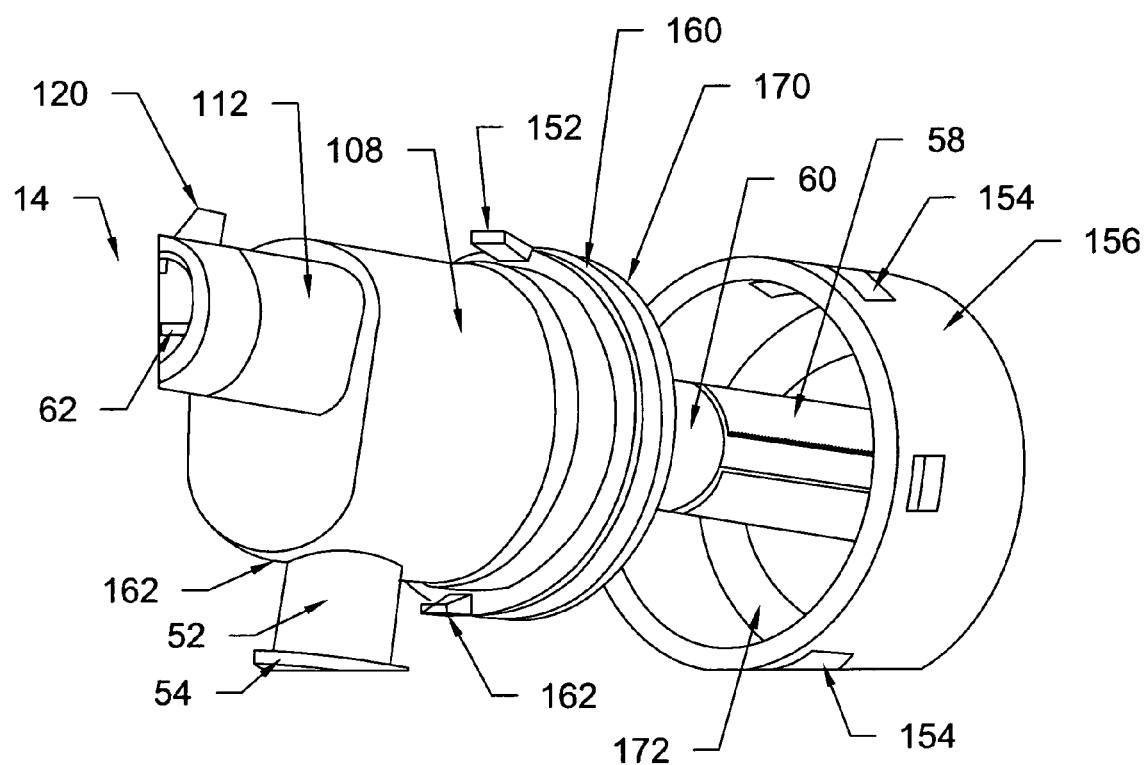
FIG. 5 illustrates the heating element housing detached from the main body.

Referring collectively to FIGS. 3-5, yet another representative form of a heating element module 14 is illustrated. In this form, a lower portion 150 (See FIG. 4) of heating element housing 108 includes a pair of outwardly protruding clips 152. When assembled into an element housing 153, clips 152 snap into a pair of clip receiving apertures or slots 154 in an upper portion 156 of element housing 153. This allows heating element housing 108 to be removably attached to element housing 153. Lower portion 150 of heating element housing 108 includes a circumferential seal recess 158. See FIGS. 5 and 6. Recess 158 includes a seal 160 that provides a fluid tight seal between heating element housing 108 and element housing 153. In one form, heating element 58 and thermostat 60 are detachably connected to heating element housing 108.

In this form, heating element housing 108 includes a fluid input port 52 that extends away from a side surface of 162 of heating element housing 108. Input port 52 includes a rib 54 and a connection portion 56. Rib 54 acts as an abutment surface when a fuel or fluid line is connected with connection portion 56. As fuel enters input port 52, it takes a ninety degree turn when it enters heating element housing 108, and then travels toward and is exposed to heating element 58 positioned in element housing 153. A distal end 164 of element housing 153 is open thereby allowing the heated fuel to travel out of element housing 153 and into filter housing 12 where it may then be filtered before being utilized during the combustion process. Element housing 153 can be connected to respective filter housing 12 using one or methods including, but not limited to, interference fit, fasteners, potting, sonic welding, snap fit, or press fit, but is preferably removably connected to filter housing 12.

Referring to FIGS. 4 and 5, during assembly a lower portion 170 of heating element housing 108 is positioned against an internal cap or ridge 172 formed in upper portion 156 of element housing 153. As previously set forth, clips 152 of heating element housing 108 fit within clip receiving slots 154 located on upper portion 156 of element housing 153. In one form, once clips 152 are positioned in clip receiving slots 154 heating element housing 108 is fixedly, yet removably, secured to element housing 153. In another form, heating element housing 108 is rotated once clips 152 are positioned in clip receiving slots 154 thereby tightening heating element housing 108 within element housing 153.

Figure 6:
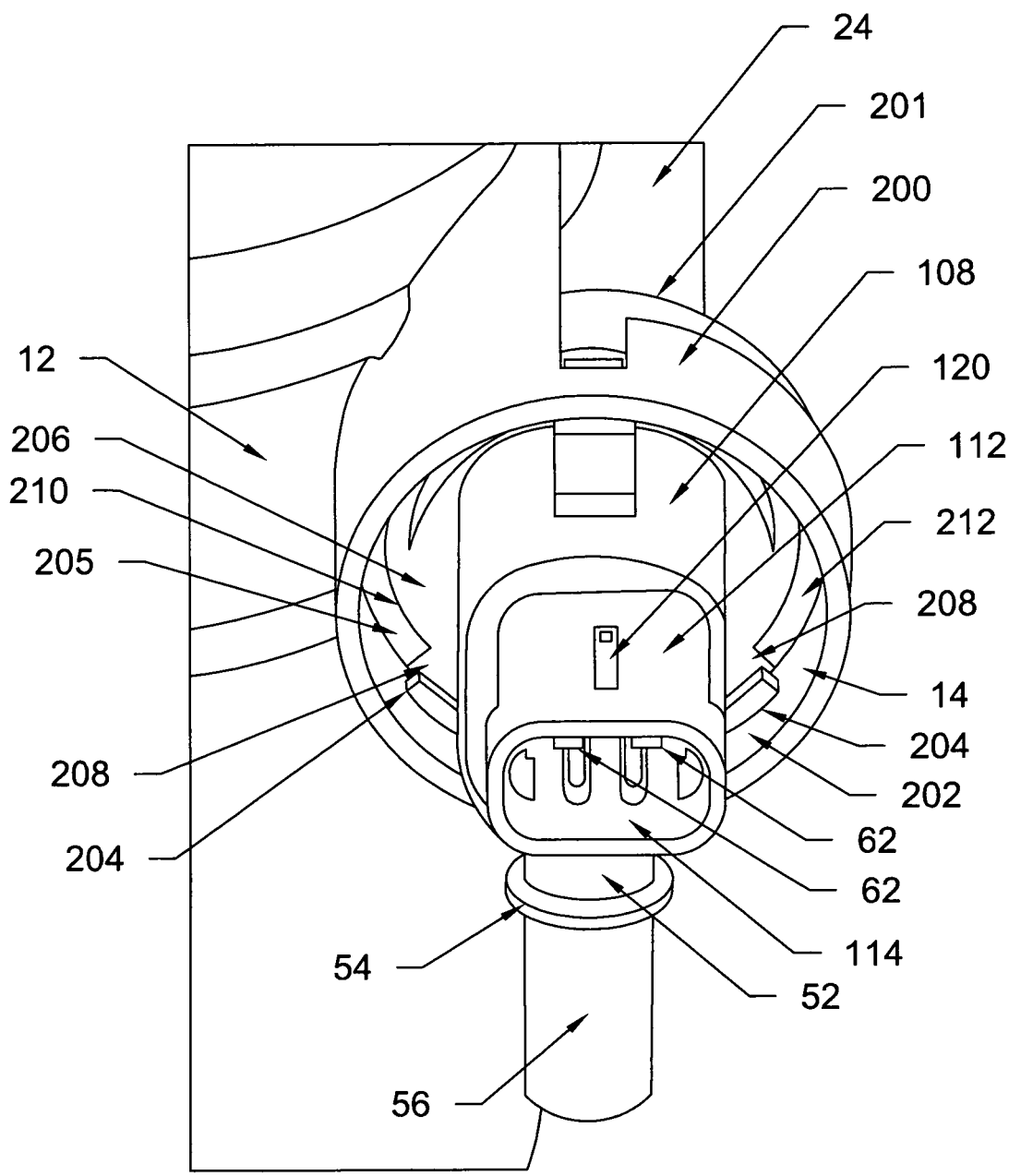
FIG. 6 illustrates another representative heating element housing connected to a filter housing.

Referring to FIG. 6, another representative form of a heating element module 14 configured to be connected to an outside surface of a filter housing 12 is illustrated. Heating element module 14 includes a heating element housing 108 that is detachably connected with a circular receiving member 200 extending from on an outside surface 201 of filter housing 12. As illustrated, receiving member 200 includes an internally recessed portion 202. Within an inside diameter of recessed portion 202 are a pair of opposing upper and lower detent segments 204 that are located above a base portion 205 of internally recessed portion 202. A circular shaped base portion 206 of heating element housing 108 include a pair of upper and lower locking members 208 that protrude outwardly from an inner inside diameter 210 of base portion 206.

When circular base portion 206 is positioned inside receiving member 200 of filter housing 12, locking members 208 fit between openings 212 located between opposing detents 204. As such, this allows locking members 208 to fit between openings 212 during assembly such that a lower surface of locking members 208 makes contact with base portion 205. When heating element housing 108 is rotated a quarter turn either clockwise or counter clockwise, heating element housing 108 is fixedly secured to main body 24. Locking members 208 engage detents 204 thereby securing heating element housing 108 within receiving member 200 of filter housing 12. As with other forms, heating element housing 108 includes a heating element 58 that extends within filter housing 12 and is utilized to heat the fuel prior to being directed to one or more filters in filter housing 12.

As illustrated, input port 52 is located on heating element housing 108 for directing fuel into heating element housing 108 and into contact with heating element 58. Although not illustrated, a heating element 58 and thermostat 60 are connected with heating element housing 108. See e.g. FIG. 7. When positioned in receiving member 200, heating element 58 and thermostat 60 protrude into filter housing 12. As would be apparent, the remaining features of this form are the same as previously discussed with other similar forms and for the sake of brevity will not be repeated.

Figure 7:
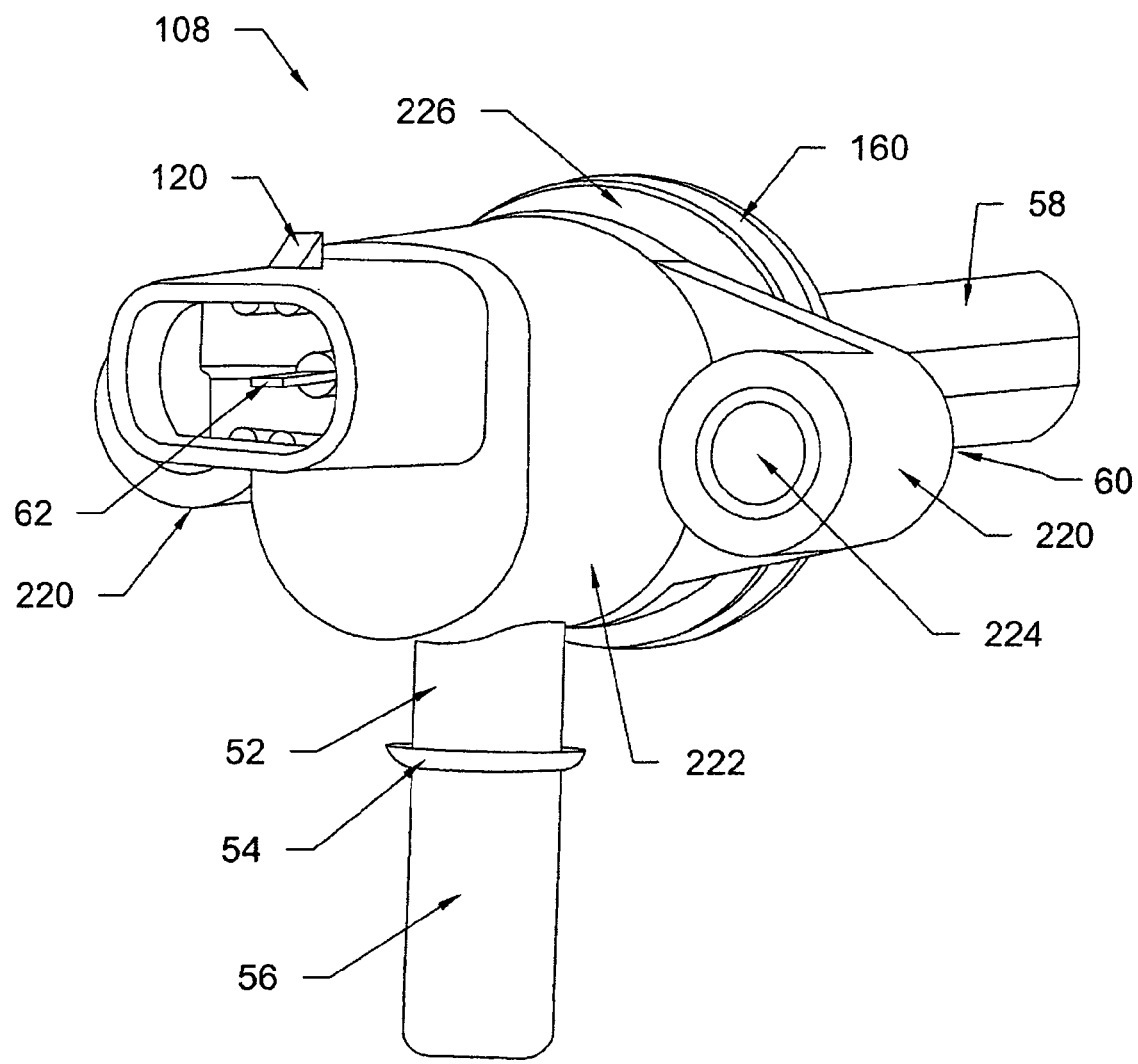
FIG. 7 illustrates another representative heating element housing configured to be connected to a filter housing.

Referring to FIG. 7, in yet another form, heating element housing 108 includes a pair of opposing lower base portions 220 that protrude outwardly from a central portion 222 of heating element housing 108. Base portions 220 include an aperture 224 that allows a fastener, such as a screw or bolt for example, to be inserted therethrough to attach heating element housing 108 to a respective filter housing 12. An engagement portion 226 of heating element housing 108 extends below base portion 220 and includes a seal 160 that provides a fluid tight seal between heating element housing 108 and filter housing 12. Fluid input port 52 extends vertically from central portion 222 of heating element housing 108. As such, in this form, as with the form illustrated in FIG. 1, heating element housing 108 is attached to an external surface of filter housing 12, but in this form, heating element 58 would extend into filter housing 12. As would be apparent, the remaining features of this form are the same as previously discussed with other forms and for the sake of brevity have not been repeated.

Figure 8:
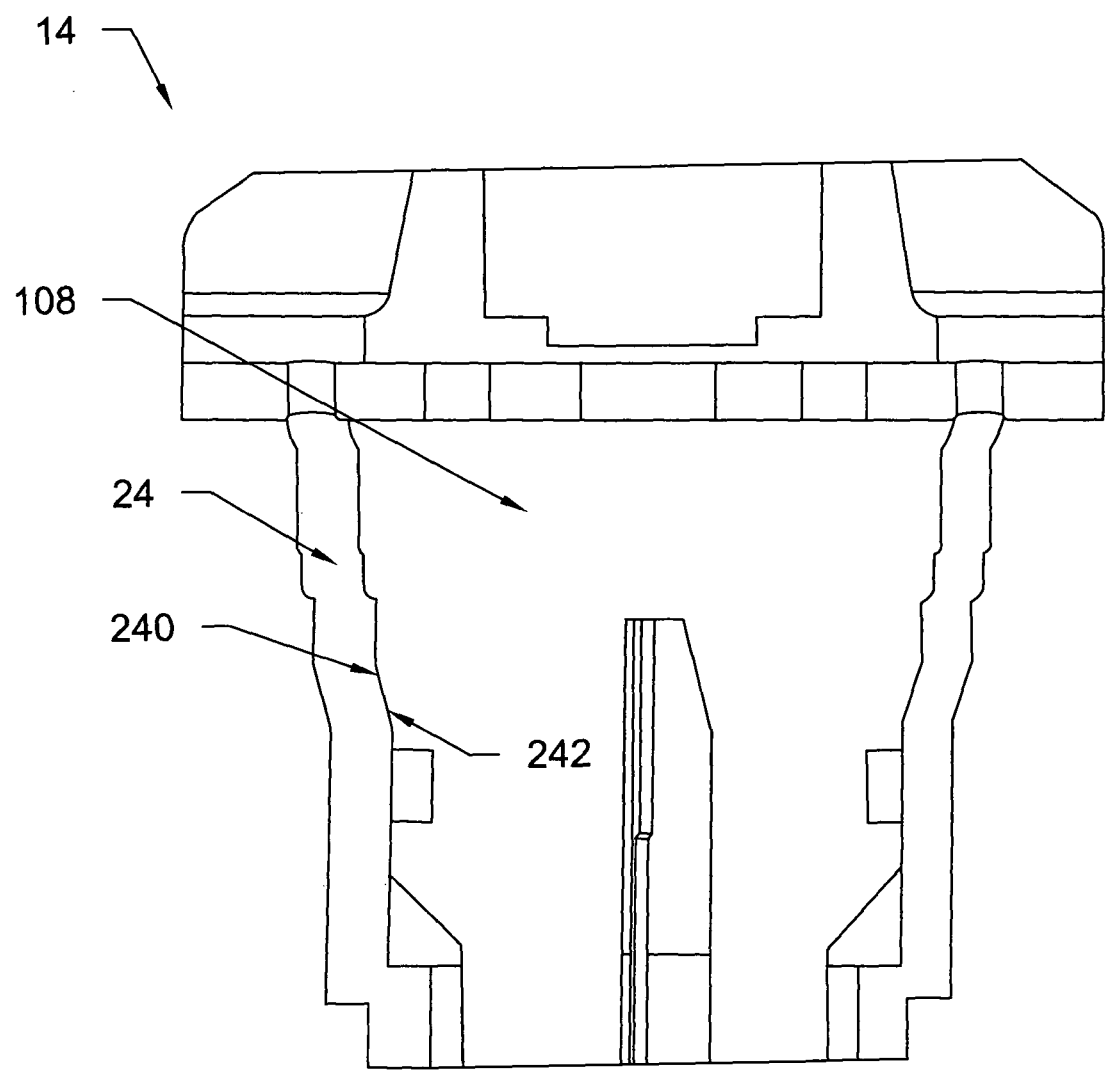
FIG. 8 illustrates a spin-welded heater module.

Referring to FIG. 8, in another representative form, main body 24 of heating element module 14 is connected with heating element housing 108 through a spin-welding process. As such, an inner wall 240 of main body 24 is welded to an outer wall 242 of heating element housing 108. Spin welding is a welding technique in which the parts to be welded are heated by friction. All other features and components may remain the same as in other embodiments of the present invention. It should be appreciated that various methods exist that could be utilized to connect the heating element housings disclosed herein to the main body. Some of the attachment methods would include but are not limited to interference fit, fasteners, potting, sonic welding, spin welding, snap fit, or press fit.

Figure 9A:
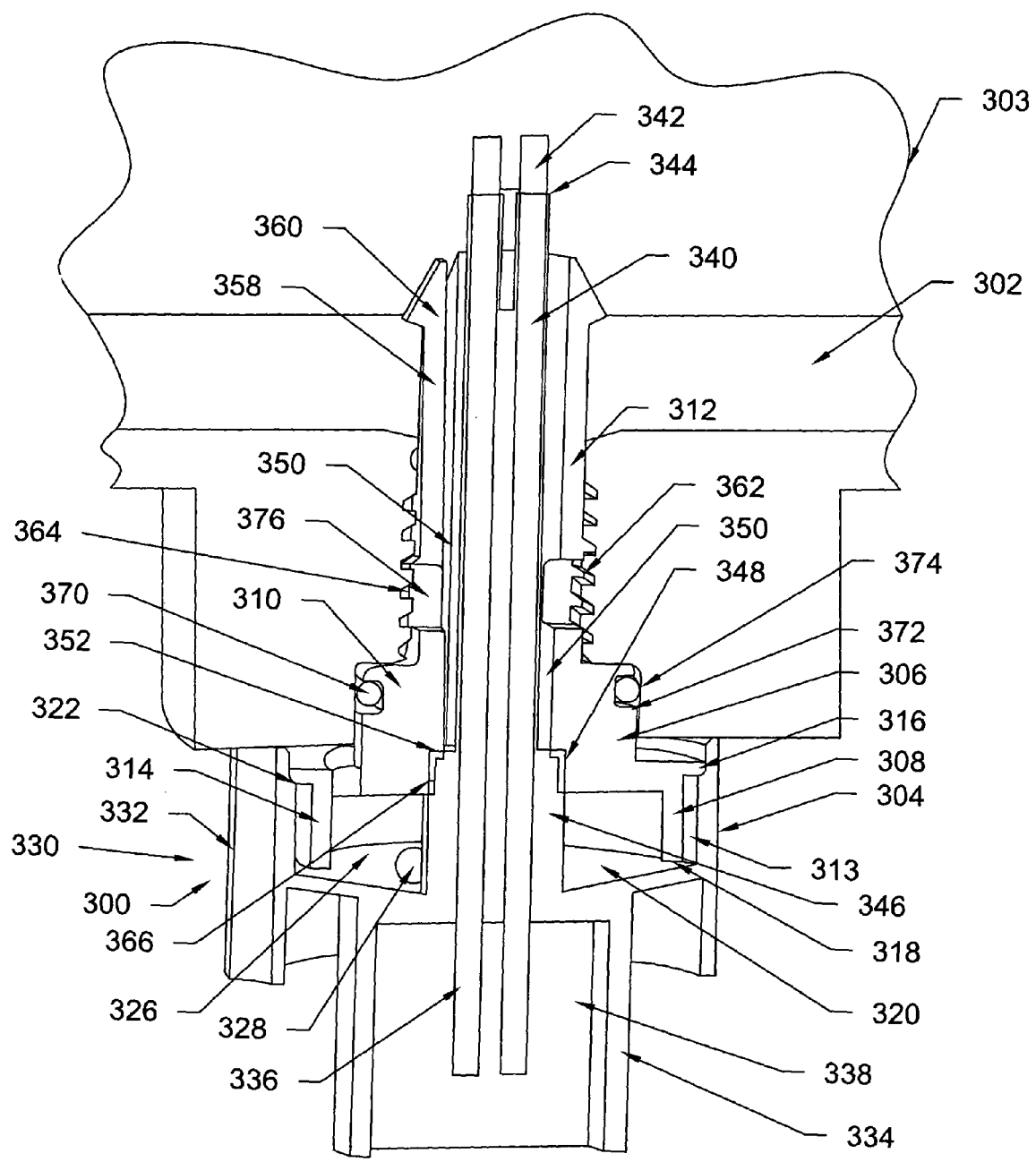
FIG. 9a is a cross-sectional view of a water-in-fuel sensor assembly or module in a closed position relative to a portion of a filter housing.
Figure 9B:
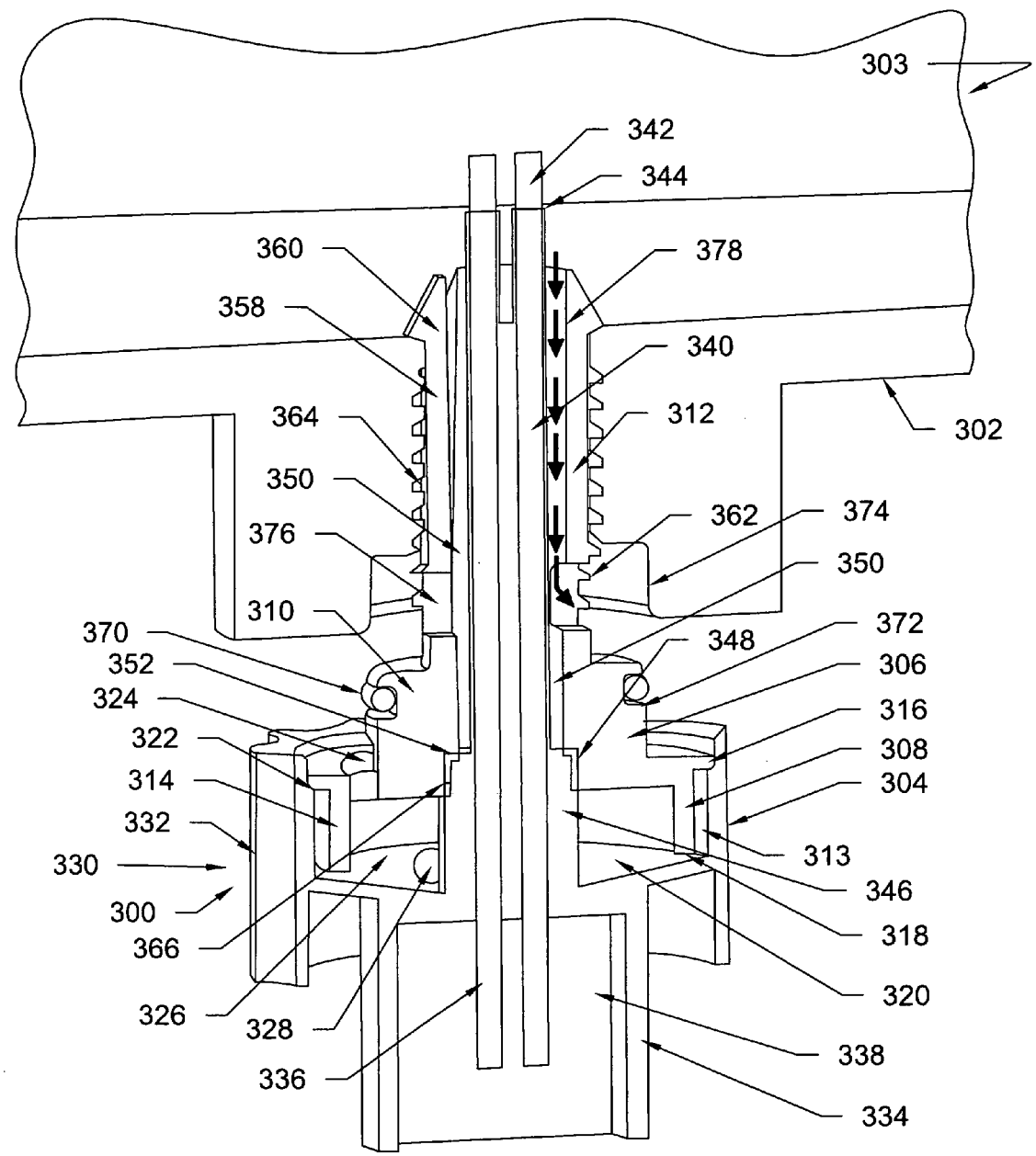
FIG. 9b is a cross-sectional view of a sensor module in an open position relative to a portion of a filter housing.
Figure 9C:
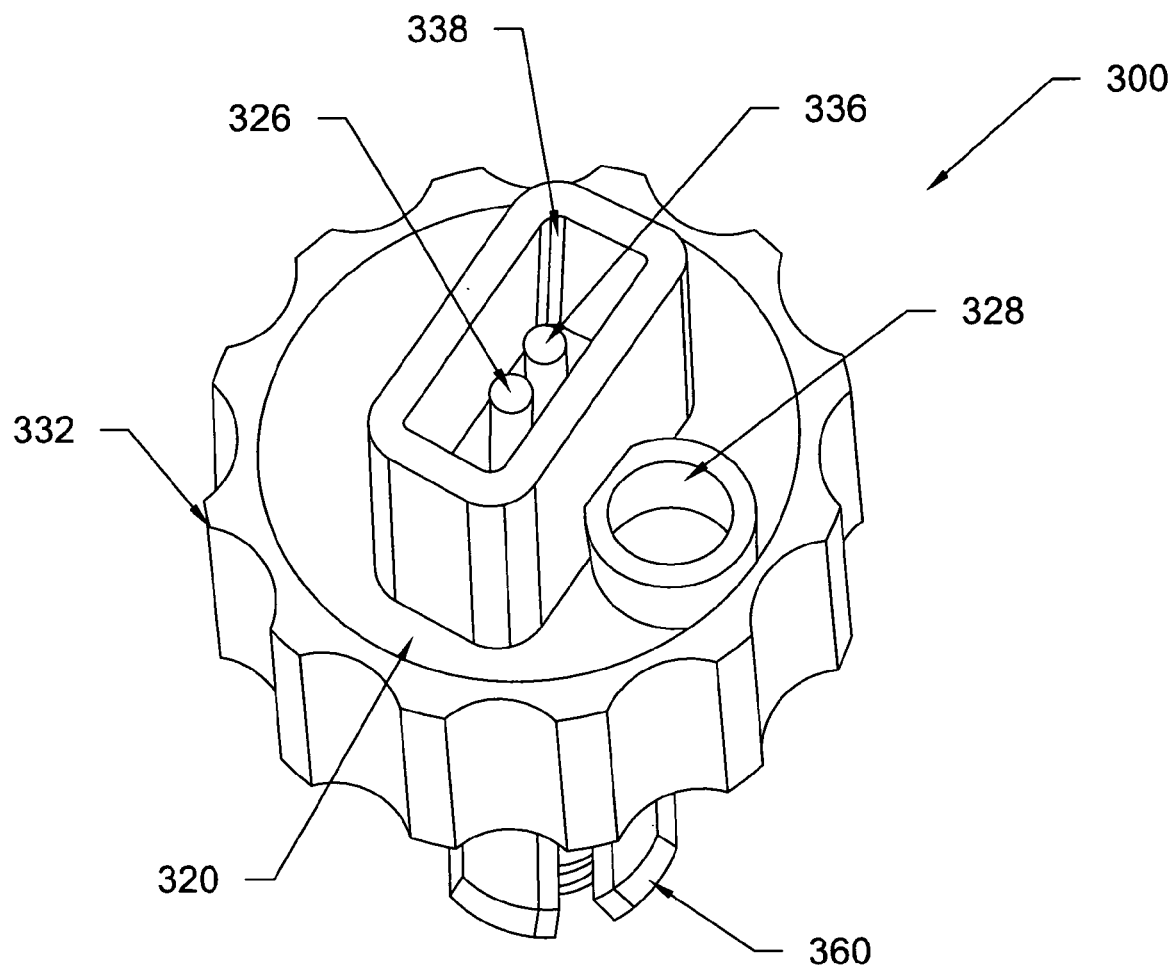
FIG. 9c is a top perspective view of the sensor module depicted in FIGS. 9a-9b.

Referring to FIGS. 9a-9c, a detachable water-in-fuel sensor module 300 connected with a filter housing 302 of a filter assembly 303 is illustrated. As described below, sensor module 300 serves as a water sensor and a drain with respect to filter assembly 303. Water-in-fuel sensor module 300 includes a cap 304 connected with a filter attachment member 306. In this form, cap 304 and attachment member 306 have a generally cylindrical shape. Attachment member 306 includes cap engagement segment 308, a middle or sealing segment 310 and an end or connection segment 312. As illustrated, cap engagement segment 308 is secured within an attachment member receive 313 defined within an inside diameter of cap 304.

Cap engagement segment 308 includes an inside member 314 and a base member 316 that extends beyond and has an outside diameter greater than inside member 314. In the illustrated form, both inside member 314 and base member 316 have a generally cylindrical shape. A lower portion 318 of inside member 314 engages an internal base portion 320 of cap 304. When positioned in cap 304, an outside edge of base member 316 engages a lip 322 formed on an upper inside surface of cap 304. Base member 316 of cap segment 308 includes an aperture 324 that allows water to flow through cap segment 308 into an internal chamber 326 formed between cap engagement segment 308 and internal base portion 320 of cap 304. Water entering internal chamber 326 is then removed from or exits chamber 326 through a cap aperture 328 in internal base portion 320 of cap 304.

An upper portion 330 of cap 304 includes an external grip 332 that allows a technician or owner to tighten or loosen sensor module 300 from filter housing 302. Cap 304 includes an electrical connector 334 that includes two sensor probes 336 that extend into an internal cavity 338 defined by electrical connector 334. A probe extension 340 extends along a vertical axis of cap 304 away from internal base portion 320 and encapsulates a portion of sensor probes 336. An end 342 of each sensor probe 336 protrudes out of a distal end 344 of probe extension 340 and is exposed to fluid contained in filter housing 302. As such, a first end of sensor probes 336 are exposed in internal cavity 338 of electrical connector 334 and a second end of sensor probes 336 are exposed in filter housing 302.

In this form, ends 342 of sensor probes 336 form a biased resistor sensor that changes resistance depending on the nature of fluid surrounding ends 342. As such, sensor probes 336 are operable to detect whether water is present in filter housing 302. A connection segment 346 of probe extension 340 fits within a first portion or cavity 348 defined by an internal channel or passage 350 of attachment member 306. First portion 348 defines an abutment surface or internal lip 352 that prevents probe extension 340 from being positioned to far into passage 350. In one form, connection segment 346 can be friction fit into first portion 348 so that cap 304, together with probes 342, can be removed from attachment member 306.

In one form, end segment 312 is formed as a chuck or collet. In this form, an upper end 358 of end segment 312 includes two or more jaw segments 360. An outer surface of end segment 312 includes external threads 362 that engage internal threads 364 of filter housing 302. As end segment 312 is screwed into filter housing 302, it causes jaw segments 360 to apply force or pressure to probe extension 340 thereby fixedly securing cap 304, and in particular probe extension 340, to filter attachment member 306. In one form, first portion 348 includes locking members 366 that allow filter attachment member 306 to rotate as cap 304 is rotated.

As illustrated, a portion of filter attachment member 306 fits within a passage 367 formed in filter housing 302. Sealing segment 310 of filter attachment member 306 includes a seal 370 that runs circumferentially around sealing segment 310. Seal 370 is placed in a seal recess 372 that is formed in and runs circumferentially around an outside portion of sealing segment 310. A portion of sealing segment 310 fits within a circular-shaped recess 374 of passage 367 in filter housing 302 when sensor module 300 is secured to filter housing 302. Seal 314 forms a fluid tight seal between attachment member 306 and filter housing 302.

If water is detected within filter housing 302, an operator or technician can remove sensor module 300 by unscrewing sensor module 300 as illustrated in FIG. 9b. Once end segment 312 is unscrewed to a predetermined position, one or more drain apertures 376 in end segment 312 become exposed and in addition, since jaw segments 360 are no longer forcefully placed in the closed position in engagement with probe extension 340, a fluid path 378 is formed between probe extension 340 and internal passage 350 thereby allowing water to exit filter housing 302. As such, water travels down fluid path 378 and exits bore 350 through apertures 376. See FIG. 9b. From there the water runs down sealing segment 310 until it reaches base portion 316 where it runs through aperture 324 and into fluid chamber 326. Once in fluid chamber 326, the water exits fluid chamber 326 through aperture 328 where it may be collected and disposed of.

Figure 10A:
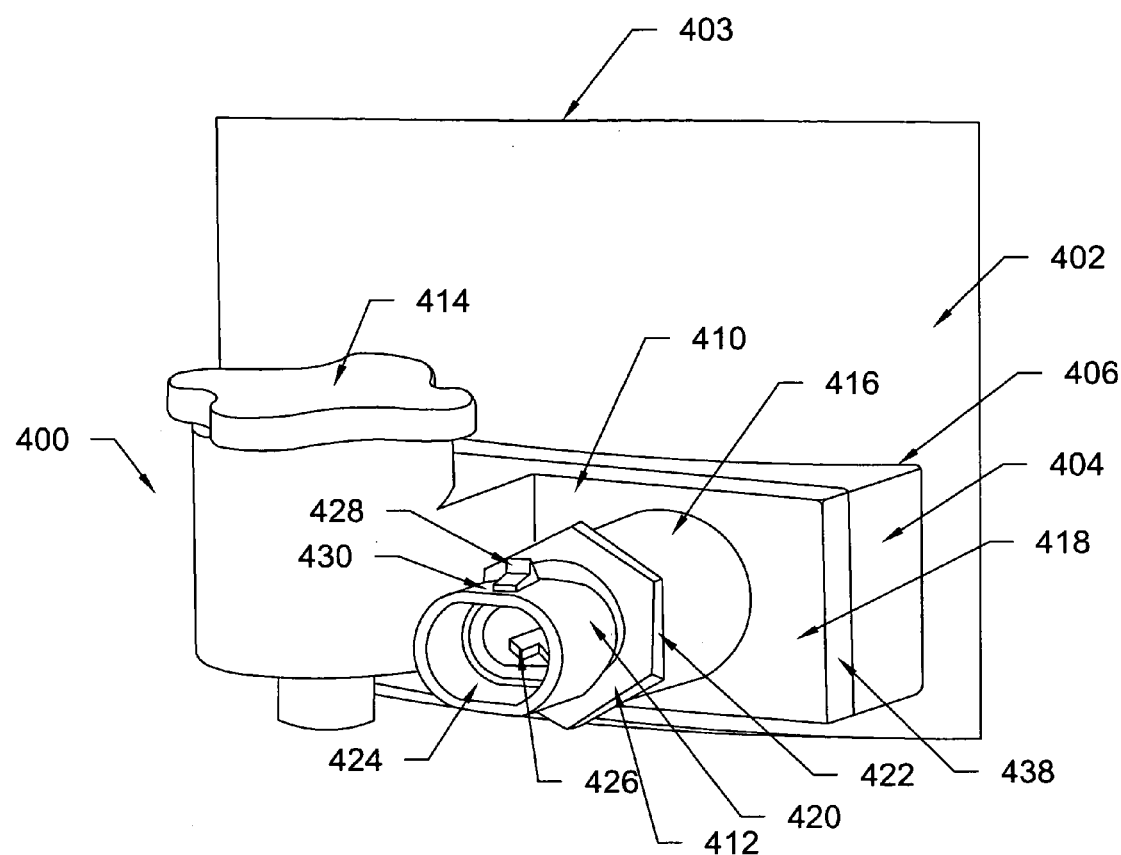
FIG. 10a is a perspective view of another water-in-fuel sensor assembly or module connected to a filter housing.

Referring to FIG. 10a, another representative detachable water-in-fuel sensor module 400 connected with a filter housing 402 of a filter assembly 403 is illustrated. In this form, sensor module 400 is connected with a sensor mounting segment or portion 404 of filter housing 402. As illustrated, in this form, sensor mounting segment 404 extends horizontally away from a side surface 406 of filter housing 402. Sensor module 400 can be connected to filter housing 402 using one or methods including, but not limited to, interference fit, fasteners, potting, sonic welding, snap fit, or press fit. In one form, sensor module 400 is connected with filter housing 402 using a method that allows sensor module 400 to be readily detached from filter housing 402 for maintenance or replacement purposes.

Referring collectively to FIGS. 10a-10d, sensor module 400 includes a sensor module housing 410, a sensor assembly 412, and a drain assembly 414. As illustrated, sensor assembly 412 and drain assembly 414 are connected with sensor module housing 410. Sensor assembly 412 can be connected to sensor module housing 410 using one or methods including, but not limited to, interference fit, fasteners, potting, sonic welding, snap fit, or press fit. In one form, sensor assembly 412 is removably connected with a connector or attachment member 416 that protrudes outwardly horizontally from a side surface 418 of sensor module housing 410. However, in another form, sensor assembly 412 may be connected directly to side surface 418 of sensor module housing 410.

Figure 10B:
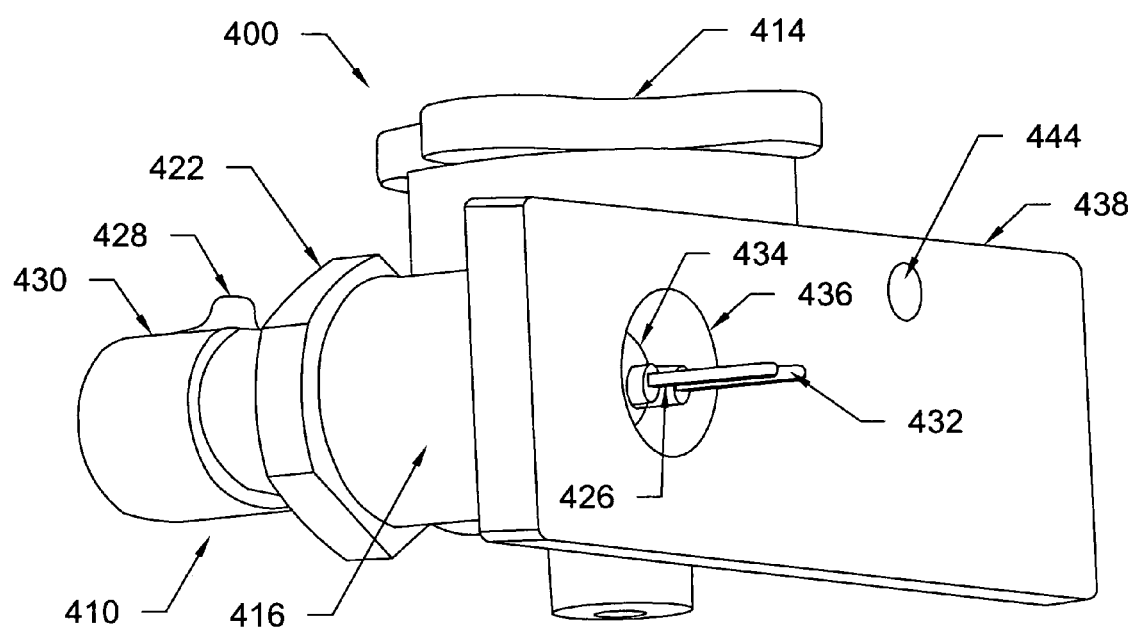
FIG. 10b is a rear view of the sensor module depicted in FIG. 10a detached from the filter housing.

Sensor assembly 412 includes an electrical connector portion 420 and a fastener 422. Electrical connector portion 420 includes an internal cavity 424, sensor probes 426 that define electrical connectors positioned in internal cavity 424, and a connector clip 428 located on an outer surface 430 of electrical connector portion 420. In the illustrated form, fastener 422 is shaped like a nut so that sensor assembly 412 can be removably attached, by screwing and unscrewing, to attachment member 416. As illustrated in FIG. 10b, end 432 of sensor probes 426 extend through sensor module housing 410 where they are exposed in filter housing 402. A sensor probe housing 434 surrounds a portion of sensor probes 426 and extends into connector member 416 of sensor module housing 410. A passageway 436 extends through connector member 416 and an attachment plate portion 438 of sensor module housing 410. As set forth in prior forms, ends 432 of sensor probes 426 are operable to detect water in filter housing 402, which as set forth in detail below, can be drained from filter housing 402 when needed.

Figure 10C:
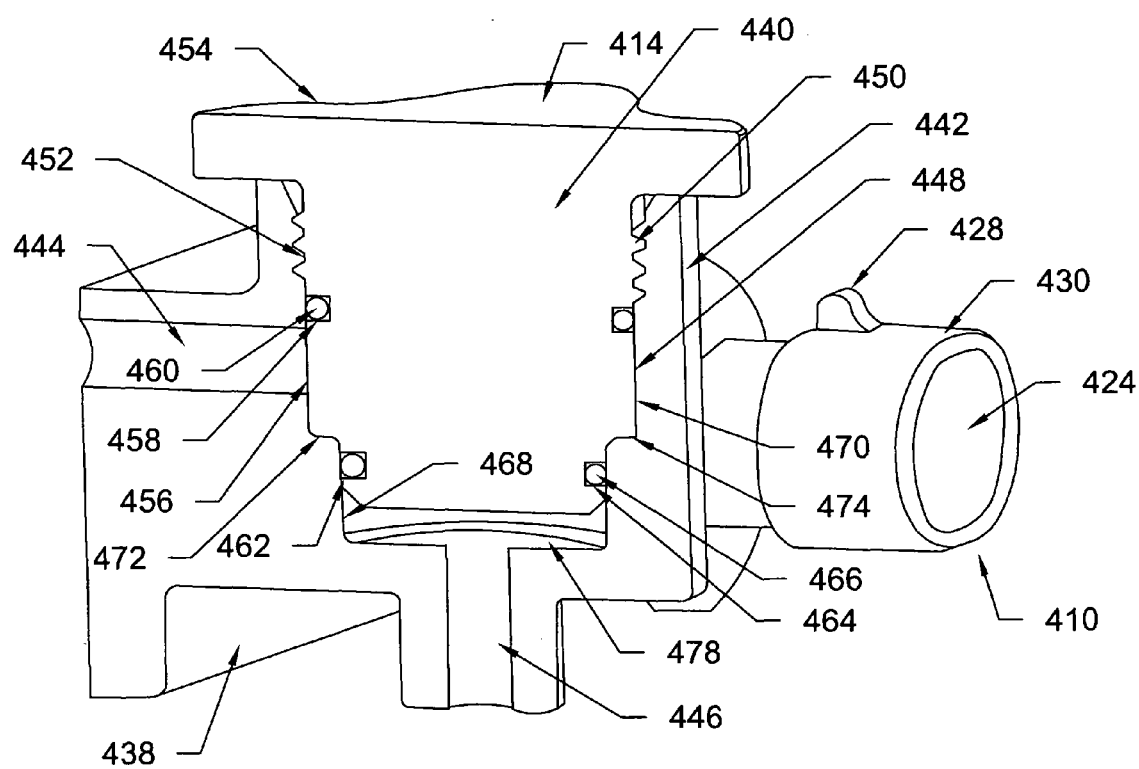
FIG. 10c is a cross-sectional view of the sensor module depicting a drain in the closed position.
Figure 10D:
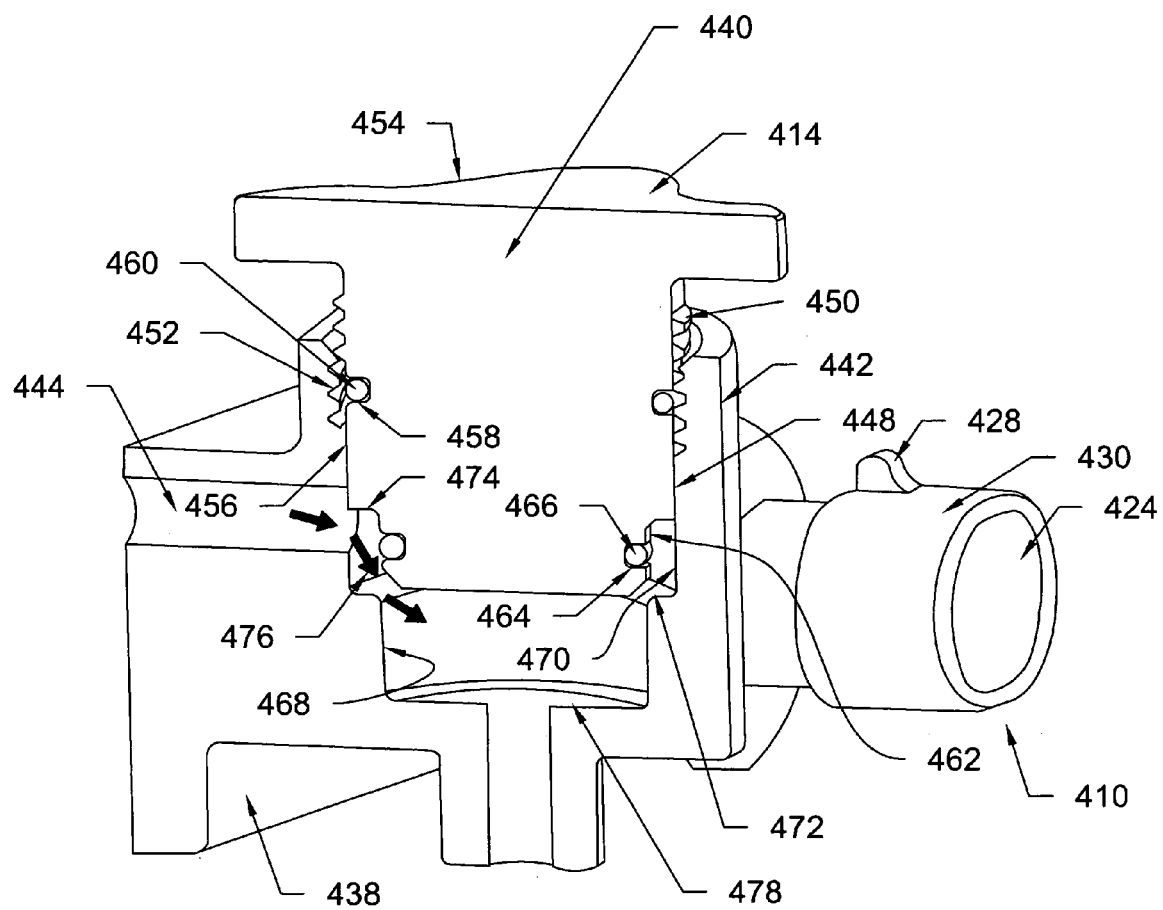
FIG. 10d is a cross-sectional view of the sensor module depicted in the open position.

Referring to FIGS. 10c and 10d, drain assembly 414 includes a drain cap 440, a drain cap attachment member 442, a first drain port 444, and a second drain port 446. Drain cap attachment member 442, first drain port 444, and second drain port 446 are formed as a part of sensor module housing 410. Drain cap 440 is positioned in an internal drain cap cavity 448 positioned along a vertical axis defined by drain cap attachment member 442. Drain cap 440 is secured in drain cap attachment member 442 such that drain cap 440 can be removed from internal drain cap cavity 448. As depicted, in one form drain cap 440 includes an upper externally threaded portion 450 that is configured to engage an upper internally threaded portion 452 of drain cap attachment member 442. Internally threaded portion 452 is located on an upper portion of internal drain cap cavity 448. An upper portion of drain cap 440 also includes a grip portion 454 that allows for easy turning of drain cap 440.

A middle portion 456 of drain cap 440 includes a first internal seal recess 458 in which a first seal 460 is positioned around middle portion 456 of drain cap 440. A lower portion 462 of drain cap 440 includes a second internal seal recess 464 in which a second seal 466 is positioned around lower portion 462 of drain cap 440. As illustrated, lower portion 462 of drain cap 440 has a smaller outside diameter than middle portion 456 of drain cap 440. In addition, a lower portion 468 of internal drain cap cavity 448 has a smaller inside diameter than an upper portion 470 of internal drain cap cavity 448. As a result, in this form an internal cavity lip 472 is formed in internal drain cap cavity 448 in which a drain cap abutment surface 474 engages when drain cap 440 is in the fully closed position.

As illustrated in FIG. 10c, when drain cap 440 is in the fully closed position, middle portion 456 of drain cap 440 blocks fluid from passing through first drain port 444. This ensures that fluid will not leave filter housing 402 through first drain port 444. First drain port 444 is exposed inside filter housing 402 when sensor module 400 is connected with filter housing 402.

Referring now to FIG. 10d, when drain cap 440 is moved to an open position, middle portion 456 of drain cap 440 no longer blocks first drain port 444 and since lower portion 462 of drain cap 440 has a smaller outside diameter, a fluid passage 476 between first input port 444 and internal drain cavity 448 is formed thereby allowing fluid, in one form water, to flow from first input port 444 into internal drain cavity 448. As illustrated, second drain port 446 runs vertically up to a lower surface 478 of internal drain cavity 448. As such, when drain cap 440 is in the open position, fluid entering internal drain cavity 448 is permitted to flow down and out of drain assembly 414. As such, once sensor probes 426 detect that unwanted fluid is present in filter housing 402, a technician or operator can loosen drain cap 440 to quickly and easily drain the unwanted fluid from filter housing 402.

Figure 11A:
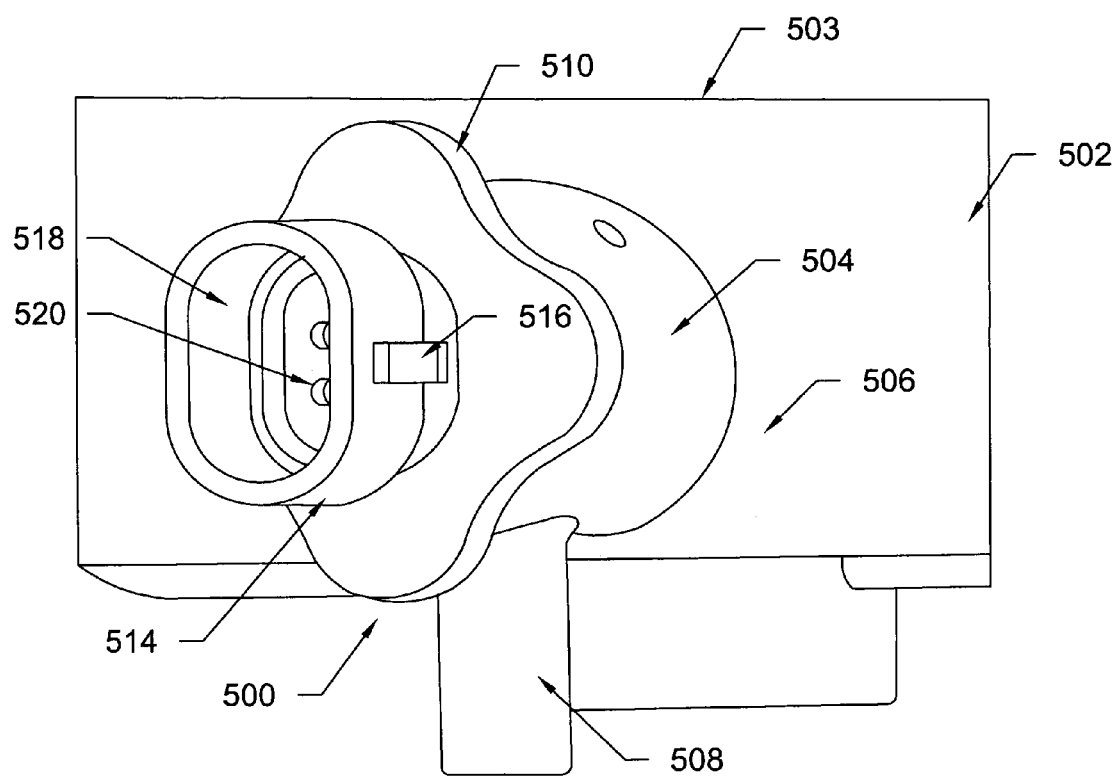
FIG. 11a is a perspective view of another representative water-in-fuel sensor assembly or module connected with a filter housing.

Referring to FIG. 11a, yet another form of a water-in-fuel sensor module 500 is illustrated that is configured to be removably connected with an existing filter housing 502 of a filter assembly 503. As set forth in detail below, in addition to comprising a water-in-fuel sensor, this form also has built-in drain capabilities allowing a technician or vehicle operator to drain fluid, in one form water, from filter housing 502. As illustrated, filter housing 502 includes a sensor module connection port 504. In this form, sensor module connection port 504 extends horizontally from a lower side surface 506 of filter housing 502. Sensor module connection port 504 also includes a drain port 508 extending vertically from a lower surface of sensor module connection 504.

Sensor module 500 includes a grip portion 510 and an electrical connector portion 512. Grip portion 510 is used to tighten and loosen sensor module 500 to connection port 504. An outside surface 514 of electrical connector 512 includes a clip 516 that is used to aid in securing a sensor cable to electrical connector 512. Electrical connector 512 defines an internal cavity 518 through which a portion of sensor probes 520 protrude outwardly so that the sensor cable can be connected to sensor probes 518.

Figure 11B:
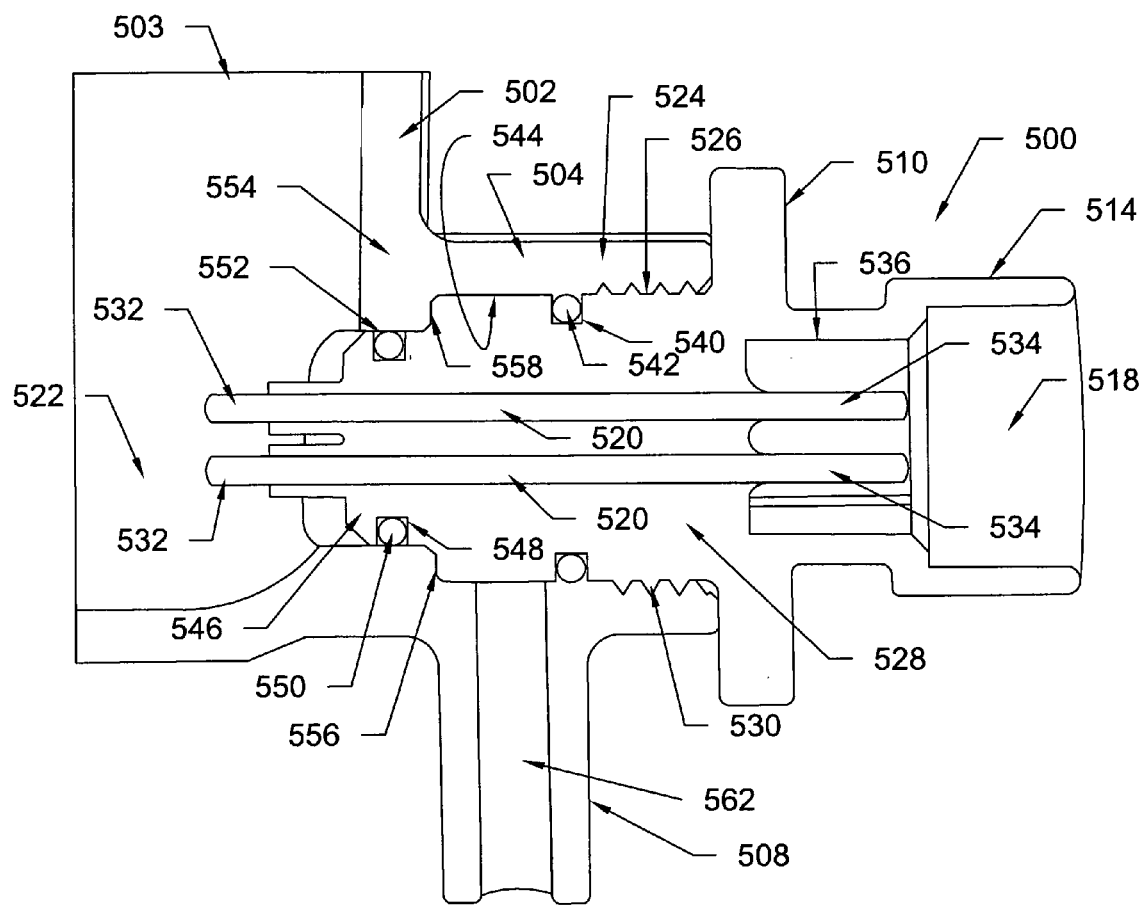
FIG. 11b is a cross-sectional view of the sensor module in the closed position relative to the filter housing.
Figure 11C:
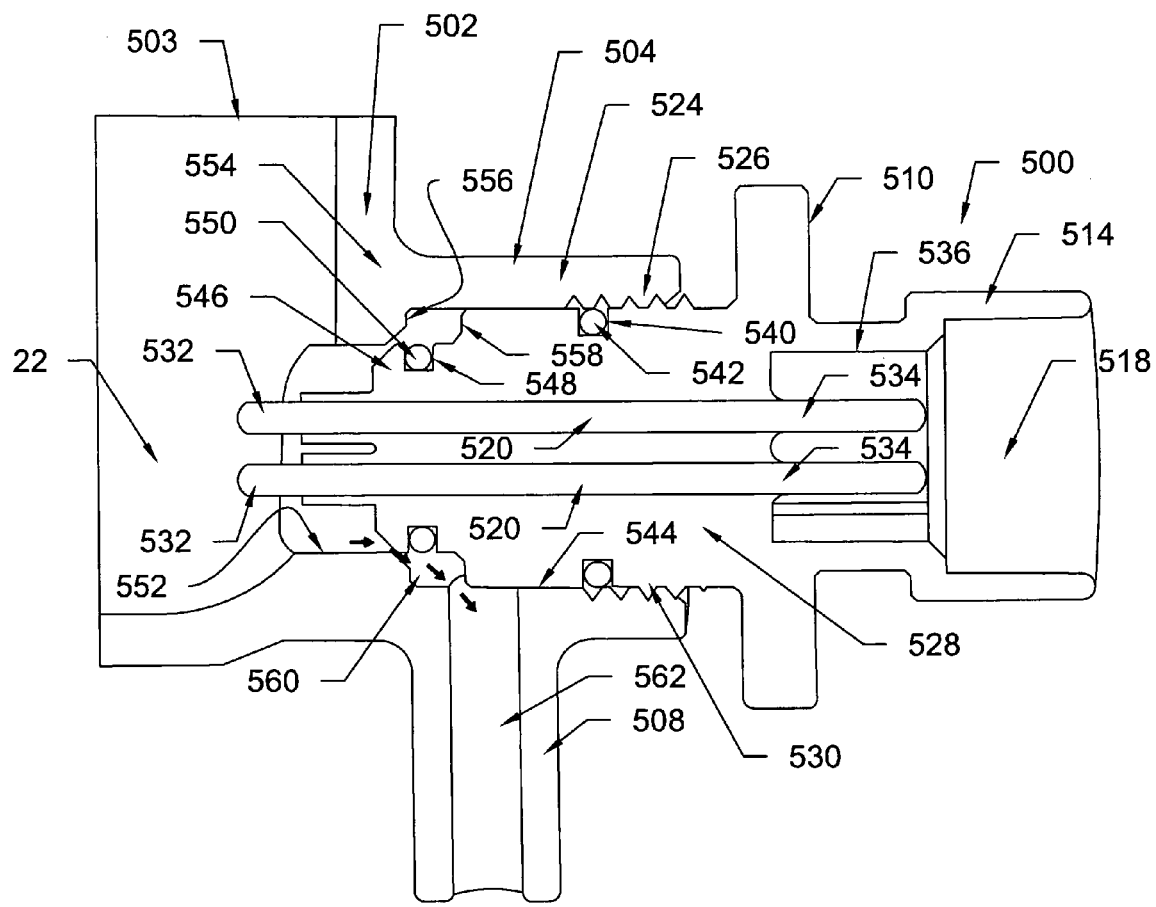
FIG. 11c is a cross-sectional view of the sensor module in the open position relative to the filter housing.

Referring to FIGS. 11b and 11c, cross-sectional views of sensor module 500 connected with filter housing 502 is illustrated. FIG. 11b illustrates sensor module 500 in a closed state such that fluid, in one form water, cannot drain through drain 508 and FIG. 11c illustrates sensor module in an open state such that fluid is permitted to drain through drain 508. As such, sensor module 500 is configured to be connected with filter housing 502 so that it is operable to detect the presence of a particular fluid, in one form water, and is also configured to be opened so that once a predetermined amount of water is detected within an internal area 522 of filter housing 502 it can be selectively drained from filter housing 502.

In this form, sensor module connection port 504 includes an end 524 that includes an internally threaded portion 526. A middle portion 528 of sensor module 500, just below grip portion 510 in this representative form, includes an externally threaded portion 530. As such, sensor module 500 attaches to sensor module connection port 504 of filter housing 502 with threads in this form. It should be appreciated that sensor module 500 is also capable of being configured to connect to sensor module connection port 504 in other ways in other forms, such as friction fit and snap fit, for example.

As illustrated, sensor probes 520 run through sensor module 500 and ends 532 of sensor probes 520 protrude outwardly from sensor module 500 and are exposed in internal area 522 of filter housing 502. The opposite ends 534 of sensor probes 520 are exposed in a probe cavity 536 formed inside electrical connector 514. As previously set forth, in one form, sensor probes 532 form a resistive based sensor that is operable to detect when water is present in internal cavity 522 of filter housing 502. In other words, as different types of fluid interact with sensor probes 532, a change in conductivity between sensor probes 532 occurs which is capable of being measured by a controller connected with sensor module 500.

Middle portion 528 of sensor module 500 includes a first circumferential seal recess 540 in which a first seal 542 is positioned to seal middle portion 528 within a first internal cavity 544 defined by sensor module connection port 504. An end portion 546 of sensor module 500, having a smaller outside diameter than middle portion 528, includes a second circumferential seal recess 548 in which a second seal 550 is positioned to seal end portion 546 within a filter housing aperture 552 in a lower side wall 554 of filter housing 502. Internal cavity 544 has a larger inside diameter than the diameter of filter housing aperture 552. As a result, a lip or abutment surface 556 is formed between internal cavity 544 and filter housing aperture 552. An abutment end 558 of middle portion 528 of sensor module 528 engages lip 556 when sensor module 500 is positioned in the fully closed position thereby preventing sensor module 500 from being positioned any further in sensor module connection port 504.

Referring to FIG. 11c, as sensor module 500 is loosened from sensor module connection port 504 and begins to back out of internal cavity 544, abutment end 558 disengages lip 556 and eventually travels back to a point where end portion 546 is no longer sealed within filter housing aperture 552. This creates a fluid path 560 from internal area 522 of filter housing 502 to passageway 562 in drain 508. As such, unwanted fluid, water in one form, is drained from internal area 522 of filter housing 502.

In some forms, the heating modules and water-in-fuel sensor modules disclosed herein would be connected with the same filter housing of a respective filter assembly. As such, both the heating modules and sensor modules would be detachable or removable from the filter assembly.

In one form, a heating module for a fluid filter assembly is disclosed. The heating module comprises an inlet port connected with a main body; an outlet port connected with a main body; a heating element positioned within said main body in a fluid flow path between said inlet port and said outlet port; and an upper and lower attachment member associated with said main body configured to removably detach said main body to an outside surface of a fluid filter housing.

Yet another aspect discloses a heating module for a filter assembly. The heating module comprises a main body; a fluid inlet port located on a lower portion of said main body; an attachment member configured to removably attach said main body to an outside surface of a fluid filter housing; a fluid outlet port extending outwardly from a side surface of said attachment member; a pair of opposing mounting members extending upwardly from an upper portion of said main body; a heating element housing removably secured to said opposing mounting members; and a heating element extending into said main body in a fluid path between said fluid inlet port and said fluid outlet port.

In yet another form, a heating module for a fluid filter assembly is disclosed. The heating module comprises a heating element housing; a fluid input port extending outwardly from a side surface of said heating element housing; at least a pair of outwardly extending clips located on a lower portion of said heating element housing; an element housing including at least a pair of clip receiving slots on an upper portion of said element housing configured to receive said pair of clips thereby securing said heating element housing to said element housing; and a heating element extending from a lower portion of said heating element housing into said element housing.

Another form discloses a heating module for a fluid filter assembly. The heating module comprises a filter housing; a receiving member located on an outer surface of said filter housing including a recessed portion having at least a pair of detents positioned above a base portion; a heating element housing having at least a pair of locking members protruding outwardly from a heating element base portion; and wherein said receiving member includes at least two openings between said pair of detents that permit said pair of locking members to be positioned against said base portion such that said heating element housing is secured in said receiving member by rotation of said heating element housing.

Yet another aspect discloses a heating module for a fluid filter assembly. The heating module comprises a housing; a fluid input port connected to a side of said housing; a heating element connected to a bottom portion of said housing and extending away from said housing; an electrical connector connected with said housing; and at least one attachment member configured to removably connect said housing to an outside surface of a filter assembly.

A further aspect discloses a fluid sensor module for a filter assembly. The fluid sensor module comprises an attachment member including a cap engagement segment, a sealing segment, and a connection segment, wherein said connection segment and said sealing segment is configured to be removably inserted into a filter housing; and a cap connected with said cap engagement segment having at least one sensor probe extending through an internal passageway through said sealing segment and said connection segment of said attachment member such that an end of said at least one probe is exposed out of an end of said connection segment.

A further aspect discloses a fluid sensor module for a filter assembly. The fluid sensor comprises a housing adapted to be connected to an outside surface of a filter housing including a sensor attachment member, a drain cap attachment member, and a drain located below said drain cap-attachment member; a sensor assembly positioned in sensor attachment member; and a drain cap positioned in said drain cap attachment member.

In yet another form, a filter assembly is disclosed comprising: a housing including a sensor connection port located on an external surface of said housing, wherein said sensor connection port defines an aperture into an internal collection cavity of said housing and a drainage port located on a lower surface of said sensor connection port; and a sensor module configured to be removably connected with said sensor connection port such that when said sensor module is in a fully tightened state in said sensor connection port at least one sensor probe is exposed in said internal collection cavity and a portion of said sensor module seals said drainage port, and wherein said sensor module is loosened to a predetermined point said drainage port is exposed thereby allowing fluid to exit said internal collection cavity through said drainage port.

Another form discloses a filter assembly comprising: a housing; a fluid heating module removably connected to an external surface of said housing; and a fluid sensor module having a sensor removably connected with said external surface of said housing, wherein said fluid sensor module includes means for draining fluid from said housing upon detection of unwanted fluid in said housing.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A fuel filter assembly, comprising:
   a heating module configured for detachable connection to a fuel filter housing of the fuel filter assembly; the heating module includes a main body, a fuel inlet port connected to the main body that feeds fuel into the main body, and a fuel outlet port connected to the main body that directs fuel to the fuel filter housing;
   a heating element housing detachably connected to the main body, the heating element housing contains a heating element positioned within said main body in a fluid flow path between said fuel inlet port and said fuel outlet port and a thermostat positioned in the fluid flow path and configured to regulate the heating element so that fuel is heated to a desired set point temperature, the heating element and the thermostat are detachable with the heating element housing from the main body;
   the heating element and the thermostat are detachably connected to the heating element housing; and
   an attachment member associated with said main body to detachably mount said main body to an outside surface of the fuel filter housing.

2. The fuel filter assembly of claim 1, wherein said fuel inlet port extends vertically from a lower surface of the main body.

3. The fuel filter assembly of claim 1, wherein said fuel outlet port extends outwardly from a side surface of said attachment member generally perpendicular to the fuel inlet port.

4. The fuel filter assembly of claim 1, wherein the heating element housing further includes an electrical connector connected with said heating element.

5. The fuel filter assembly of claim 1, further comprising a fluid sensor module configured for detachable connection to the fuel filter housing of the fuel filter assembly, the fluid sensor module including:
   an attachment member including a cap engagement segment, a sealing segment, and a connection segment, wherein said connection segment and said sealing segment are configured to be removably inserted into the fuel filter housing; and
   a cap connected with said cap engagement segment having at least one sensor probe extending through an internal passageway through said sealing segment and said connection segment of said attachment member such that an end of said at least one probe is exposed out of an end of said connection segment.

6. The fuel filter assembly of claim 5, wherein said cap includes a probe extension and a connection segment that house said at least one probe.

7. The fuel filter assembly of claim 5, wherein said cap includes a connection segment that fits within a cavity in said sealing segment of said attachment member.

8. The fuel filter assembly of claim 5, wherein a base member of said cap engagement segment engages an internal lip of said cap.

9. The fuel filter assembly of claim 5, wherein said sealing segment is configured to fit within a first cavity of said filter housing.

10. The fuel filter assembly of claim 5, wherein said connection segment comprises a collet with two or more jaw segments, and threads on an outer surface of the jaw segments.

11. The fuel filter assembly of claim 5, wherein a base portion of said cap engagement segment includes an aperture.

12. The fuel filter assembly of claim 5, wherein a fluid cavity is formed between a lower portion of said cap engagement member and an internal base portion of said cap.

13. The fuel filter assembly of claim 5, wherein a lower portion of said connection segment of said attachment member includes at least one aperture.

* * * * *

UNITED STATES PATENT AND TRADEMARK OFFICE
CERTIFICATE OF CORRECTION

| | | |
|---|---|---|
| PATENT NO. | : 8,496,816 B2 | |
| APPLICATION NO. | : 12/284685 | |
| DATED | : July 30, 2013 | |
| INVENTOR(S) | : True-Dahl et al. | |

It is certified that error appears in the above-identified patent and that said Letters Patent is hereby corrected as shown below:

Title Page, Item 75, Inventors: For the third named inventor, delete "Arnuad LeVen" and insert --Arnaud LeVen--.

Signed and Sealed this
Nineteenth Day of November, 2013

Teresa Stanek Rea
*Deputy Director of the United States Patent and Trademark Office*